US010545132B2

(12) United States Patent
Guthrie et al.

(10) Patent No.: US 10,545,132 B2
(45) Date of Patent: Jan. 28, 2020

(54) PHYSIOLOGICAL MONITORING SYSTEM COMMUNICATING WITH AT LEAST A SOCIAL NETWORK

(71) Applicant: LifeScan Scotland Limited, Inverness-shire (GB)

(72) Inventors: Brian Guthrie, Inverness-shire (GB); David Elder, Inverness-shire (GB); Graeme Pringle, Inverness-shire (GB); Damian Edward Haydon Baskeyfield, Nairnshire (GB)

(73) Assignee: LifeScan IP Holdings, LLC, Malvern, PA (US)

( * ) Notice: Subject to any disclaimer, the term of this patent is extended or adjusted under 35 U.S.C. 154(b) by 819 days.

(21) Appl. No.: 13/927,077

(22) Filed: Jun. 25, 2013

(65) Prior Publication Data

US 2014/0374276 A1    Dec. 25, 2014

(51) Int. Cl.
*G01N 33/487*    (2006.01)
*G16H 10/60*    (2018.01)
*A61B 5/00*    (2006.01)

(52) U.S. Cl.
CPC ..... *G01N 33/48792* (2013.01); *A61B 5/0002* (2013.01); *G16H 10/60* (2018.01)

(58) Field of Classification Search
CPC .... G06F 19/322–345; G01N 33/48792; G01N 33/49; G01N 33/492;

(Continued)

(56) References Cited

U.S. PATENT DOCUMENTS 5,897,493 A    4/1999 Brown
6,032,119 A    2/2000 Brown et al.
(Continued)

FOREIGN PATENT DOCUMENTS

JP    2009539491 A    11/2009
JP    2011501683 A    1/2011
(Continued)

OTHER PUBLICATIONS

"Frequently Asked Questions on iBGStar® and BGStar®", retrieved May 30, 2013 from http://www.bgstar.com/web/faq, 4 pages.
(Continued)

*Primary Examiner* — Maris R Kessel

(57) ABSTRACT

A physiological measurement system includes a biosensor providing a signal for a fluid sample. A processor determines a physiological parameter in the form of an analyte concentration using the signal from the biosensor. A network interface conveys data between the processor and a social network. The processor can transmit a query for analyte-data-request records to the social network, receive an indication of an analyte-data-request record from the social network, and transmit the determined analyte data or physiologic data to the social network in response to the indication. The processor can alternatively retrieve user credentials from a storage device, transmit the credentials and the analyte data to the social network, retrieve from the social network different-user response data corresponding to the transmission, and present an indication of the response data. Methods for processing analyte or physiologic data are also described. Various methods include transmitting credentials and the stored analyte or physiologic data to the social network.

16 Claims, 5 Drawing Sheets

(58) Field of Classification Search
CPC .... G01N 27/327–3274; G08C 2201/30; A61B 5/0002; G16H 10/60
See application file for complete search history.

(56) References Cited

U.S. PATENT DOCUMENTS

| | | | |
|---|---|---|---|
| 6,151,586 A | 11/2000 | Brown | |
| 6,241,862 B1 * | 6/2001 | McAleer | C12Q 1/002 204/403.05 |
| 6,381,577 B1 | 4/2002 | Brown | |
| 6,605,038 B1 | 8/2003 | Teller et al. | |
| 6,643,385 B1 | 11/2003 | Bravomalo | |
| 6,684,090 B2 | 1/2004 | Ali et al. | |
| 6,734,858 B2 | 5/2004 | Attar et al. | |
| 6,761,697 B2 | 7/2004 | Rubinstenn et al. | |
| 6,817,979 B2 | 11/2004 | Nihtila | |
| 6,972,775 B1 | 12/2005 | Haakonsen | |
| 7,229,288 B2 | 6/2007 | Stuart et al. | |
| 7,305,348 B1 | 12/2007 | Brown | |
| 7,618,260 B2 | 11/2009 | Daniel et al. | |
| 7,693,836 B2 | 4/2010 | Brave et al. | |
| 7,711,506 B2 | 5/2010 | Burdett et al. | |
| 7,756,722 B2 | 7/2010 | Levine et al. | |
| 7,843,323 B2 | 11/2010 | Lim et al. | |
| 7,925,973 B2 | 4/2011 | Allaire et al. | |
| 7,937,465 B2 | 5/2011 | Firminger et al. | |
| 7,941,326 B2 | 5/2011 | Brown | |
| 7,945,632 B2 | 5/2011 | Firminger et al. | |
| 7,967,731 B2 | 6/2011 | Kil | |
| 7,996,189 B2 | 8/2011 | Kaplan | |
| 8,004,396 B2 | 8/2011 | Liu et al. | |
| 8,005,948 B2 | 8/2011 | Firminger et al. | |
| 8,066,640 B2 | 11/2011 | Angelides | |
| 8,092,226 B2 | 1/2012 | Findlay | |
| 8,095,192 B2 | 1/2012 | Baker, Jr. et al. | |
| 8,133,176 B2 | 3/2012 | Porges et al. | |
| 8,180,592 B2 | 5/2012 | Yuen et al. | |
| 8,214,007 B2 | 7/2012 | Baker et al. | |
| 8,275,649 B2 | 9/2012 | Zheng et al. | |
| 8,291,027 B2 | 10/2012 | McAleer et al. | |
| 8,347,326 B2 | 1/2013 | Weitzenfeld et al. | |
| 8,398,546 B2 | 3/2013 | Pacione et al. | |
| 2004/0133079 A1 | 7/2004 | Mazar et al. | |
| 2005/0131736 A1 | 6/2005 | Nelson et al. | |
| 2005/0245839 A1 | 11/2005 | Stivoric et al. | |
| 2006/0089543 A1 | 4/2006 | Kim et al. | |
| 2007/0027382 A1 | 2/2007 | Berman et al. | |
| 2007/0123754 A1 | 5/2007 | Cuddihy et al. | |
| 2007/0220006 A1 | 9/2007 | Elletson et al. | |
| 2007/0251836 A1 | 11/2007 | Hsu | |
| 2008/0146890 A1 | 6/2008 | Leboeuf et al. | |
| 2008/0154099 A1 | 6/2008 | Aspel et al. | |
| 2009/0103469 A1 | 4/2009 | Smith et al. | |
| 2009/0124866 A1 | 5/2009 | Guillama et al. | |
| 2009/0326981 A1 | 12/2009 | Karkanias et al. | |
| 2010/0315225 A1 | 12/2010 | Teague | |
| 2010/0317937 A1 | 12/2010 | Kuhn et al. | |
| 2011/0046977 A1 | 2/2011 | Goodnow et al. | |
| 2011/0046981 A1 | 2/2011 | Metzler et al. | |
| 2011/0074596 A1 | 3/2011 | Frohlick et al. | |
| 2011/0125680 A1 | 5/2011 | Bosworth et al. | |
| 2011/0230732 A1 * | 9/2011 | Edman | A61B 5/4869 600/301 |
| 2011/0320130 A1 | 12/2011 | Valdes et al. | |
| 2012/0059230 A1 | 3/2012 | Teller et al. | |
| 2012/0094600 A1 | 4/2012 | Dellostritto et al. | |
| 2012/0124122 A1 | 5/2012 | el Kaliouby et al. | |
| 2012/0130910 A1 * | 5/2012 | Al-Alami | G06Q 30/016 705/304 |
| 2012/0149996 A1 | 6/2012 | Stivoric et al. | |
| 2012/0195250 A1 | 8/2012 | Jain et al. | |
| 2012/0197621 A1 * | 8/2012 | Jain | G06F 19/3418 703/11 |
| 2012/0220835 A1 | 8/2012 | Chung | |
| 2012/0238853 A1 * | 9/2012 | Arefieg | A61B 5/0022 600/365 |
| 2012/0239743 A1 | 9/2012 | Gunsay et al. | |
| 2012/0264446 A1 | 10/2012 | Xie et al. | |
| 2012/0265024 A1 | 10/2012 | Shrivastav et al. | |
| 2012/0266191 A1 | 10/2012 | Abrahamsson et al. | |
| 2012/0271121 A1 | 10/2012 | Della Torre et al. | |
| 2012/0271655 A1 | 10/2012 | Knobel et al. | |
| 2012/0314871 A1 | 12/2012 | Koga | |
| 2012/0316406 A1 | 12/2012 | Rahman et al. | |
| 2012/0323496 A1 | 12/2012 | Burroughs et al. | |
| 2013/0031179 A1 | 1/2013 | Christakis et al. | |
| 2013/0091208 A1 * | 4/2013 | Rajakarunanayake | H04W 4/21 709/204 |
| 2013/0110760 A1 | 5/2013 | Baughman et al. | |
| 2013/0217982 A1 * | 8/2013 | Behzadi | G06F 19/3456 600/302 |

FOREIGN PATENT DOCUMENTS

| | | |
|---|---|---|
| JP | 2012157700 A | 8/2012 |
| JP | 2012529926 A | 11/2012 |
| JP | 5120989 B1 | 1/2013 |
| JP | 2013005021 A | 1/2013 |
| WO | 2008048452 A2 | 4/2008 |
| WO | 2010144720 A1 | 12/2010 |
| WO | 2012068193 A2 | 5/2012 |

OTHER PUBLICATIONS

"iBGStar® Blood Glucose Meter," retrieved May 30, 2013 from http://www.bgstar.com/web/ibgstar, 3 pages.

International Search Report and Written Opinion issued in related International Patent Application No. PCT/EP2014/063309, dated Dec. 4, 2014, 14 pages.

Anonymous: "Biosensor—Wikipedia, the free encyclopedia", Jun. 9, 2013 (Jun. 9, 2013), XP055154591, Retrieved from the Internet: URL: http://en.wikipedia.org/w/index.php?title=Biosensor&oldid=559059305.

Notice of Reasons for Rejection issued in related Japanese Patent Application No. 2016-520540, dated Mar. 27, 2018, 6 pages (with English translation).

Notice of Reasons for Rejection issued in corresponding Japanese Patent Application No. 2016-520540, dated Oct. 23, 2018, 5 pages (with English Translation).

Search Report issued in corresponding Russia Patent Application No. 2016101992, dated Apr. 11, 2018, 4 pages (with English translation).

Official Action issued in corresponding Russia Patent Application No. 2016101992, dated Apr. 12, 2018, 15 pages (with English translation).

Notification issued in corresponding Russia Patent Application No. 2016101992, dated Dec. 11, 2018, 14 pages (with English translation).

Joseph A. Cafazzo et. al. Design of an mHealth App for the Self-management of Adolescent Type 1 Diabetes: A Pilot Study. J Med Internet Res. May-Jun. 2012; 14(3): e70.

* cited by examiner

PHYSIOLOGICAL MONITORING SYSTEM COMMUNICATING WITH AT LEAST A SOCIAL NETWORK

TECHNICAL FIELD

This application relates generally to the field of analyte or physiologic measurement systems and more specifically to an analyte or physiologic measurement system that conveys data over an interface with at least one social network (or equivalent).

BACKGROUND

Diabetes mellitus is a chronic metabolic disorder caused by an inability of the pancreas to produce sufficient amounts of the hormone insulin, resulting in the decreased ability of the body to metabolize glucose. This failure leads to hyperglycemia, i.e. the presence of an excessive amount of glucose in the blood plasma. Persistent hyperglycemia and hypoinsulinemia have been associated with a variety of serious symptoms and life-threatening long-term complications such as dehydration, ketoacidosis, diabetic coma, cardiovascular diseases, chronic renal failure, retinal damage and nerve damages with the risk of amputation of extremities. Because restoration of endogenous insulin production is not yet possible, a permanent therapy is necessary which provides constant glycemic control in order to always maintain the level of blood glucose ("BG") within normal limits. Such glycemic control is achieved by regularly supplying external insulin to the body of the patient to thereby reduce the elevated levels of blood glucose.

External biologic agents such as insulin can be administered as multiple daily injections of a mixture of rapid and intermediate-acting drugs via a hypodermic syringe. Improved glycemic control can be achieved by the so-called "intensive hormone" therapy which is based on multiple daily injections, including one or two injections per day of a long acting hormone for providing basal hormone and additional injections of rapidly acting hormone before each meal in an amount proportional to the size of the meal. Although traditional syringes have at least partly been replaced by insulin pens, the frequent injections are nevertheless very inconvenient for the patient, particularly those who are incapable of reliably self-administering injections. For some patients, substantial improvements in diabetes therapy have been achieved by the development of drug delivery devices, such as pumps, that relieve the patient of the need for syringes or drug pens and the need to administer multiple daily injections.

In addition, delivery directly into the intraperitoneal space or intravenously can be achieved by drug delivery devices. Drug delivery devices can be constructed as an implantable device for subcutaneous arrangement or can be constructed as an external device with an infusion set for subcutaneous infusion to the patient via the transcutaneous insertion of a catheter, cannula or a transdermal drug transport, such as through a patch. External drug delivery devices are typically mounted on clothing, hidden beneath or inside clothing, or mounted on the body, and are generally controlled via a user interface built into the device or arranged on a separate remote device.

Blood or interstitial glucose monitoring can be used to achieve acceptable glycemic control. The determination of blood glucose concentration can be performed by means of an episodic measuring device, such as a hand-held electronic meter, that receives blood samples on enzyme-based test strips and calculates the blood glucose value based on an electrochemical reaction of the blood and the enzyme. Continuous glucose monitoring (CGM) using a sensor inserted into or implanted in the body can also be used.

Many patients use episodic measuring of blood glucose. This approach is straightforward, but requires regular attention from the patient. Some patients have formed online electronic communities, such as the Web site diabetes.co.uk, to support and encourage each other in performing measurements and injections regularly. However, these sites are inaccessible when the patient is not within reach of a computer with a network connection. Moreover, these sites can be very large and thus forbidding to navigate. As of this writing, for example, the diabetes.co.uk Web site claims 62,560 members contributing to discussion forums with 34,698 forum topics holding a total of 345,280 individual forum posts.

SUMMARY OF THE DISCLOSURE

In one embodiment, therefore, we have devised a physiological measurement system. The system may include the following components:
  a) a biosensor having at least one electrode responsive to an electrochemical reaction between a fluid sample and an enzyme disposed on the at least one electrode, so that the biosensor provides a signal corresponding to a physiological parameter in the form of an analyte concentration in the fluid sample;
  b) a processor connected to the biosensor and configured to receive the signal from the biosensor and automatically determine analyte data using the signal; and
  c) a network interface connected to the processor and configured to selectively convey data between the processor and a social network via a communications such that the processor transmits a query for analyte-data-request records to the social network, receives an indication of an analyte-data-request record from the social network, and transmits the determined analyte data to the social network in response to the indication.

In another embodiment, we have devised a physiological measurement system for use by a user. The system may include the following components:
  a) a biosensor having at least one electrode responsive to an electrochemical reaction between a fluid sample and an enzyme disposed on the at least one electrode, so that the biosensor provides a signal corresponding to a physiological parameter in the form of an analyte concentration in the fluid sample;
  b) a processor connected to the biosensor and configured to receive the signal from the biosensor and automatically determine analyte data using the signal;
  c) a network interface connected to the processor and configured to selectively convey data between the processor and a social network via a communications link;
  d) a storage device that stores credentials of the user; and
  e) a user interface operative to present information to the user, so that the processor retrieves the credentials from the storage device, transmits the credentials and the analyte data to the social network, retrieves from the social network response data corresponding to the transmission, the response data corresponding to a second user different from the user, and presents an indication of the response data using the user interface.

In another embodiment, we have devised a method for processing analyte data. The method can be achieved by automatically performing the following steps using a processor:

receiving analyte data of a user from a biosensor that detects an analyte level in a bodily fluid of the user;

storing the received analyte data in a storage device;

transmitting to a social network a query for analyte-data-request records;

receiving from the social network an indication of an analyte-data-request record;

retrieving credentials of the user from the storage device; and in response to the received indication, transmitting the credentials and the stored analyte data to the social network.

These embodiments exemplary of the present invention provide improved communications between diabetic patients, and increased usability of social networks by diabetic patients. Various embodiments relieve patients of the need to manually check for inquiries regarding their blood sugar. Various embodiments relieve patients of the need to manually view responses to posts they make to a social network. Various embodiments automatically locate relevant posts so that users are not required to navigate large, complex forum or Web-site structures.

Accordingly, in any of the embodiments described earlier, the following features may also be utilized in various combinations with the previously disclosed embodiments. For example, the physiological measurement can include a storage device that stores user credentials, so that the processor retrieves the user credentials from the storage device and transmits them to the social network in association with the transmission of the determined analyte data; a user interface and a storage device that stores respective user credentials for a plurality of social networks, so that the processor presents a menu of the plurality of social networks to a user of the system via the user interface, receives a selection of one of the plurality of social networks via the user interface, retrieves the user credentials corresponding to the selection from the storage device, and transmits the retrieved user credentials with the determined analyte data; a user interface and a housing holding the biosensor, the processor, the network interface, and the user interface; a user interface, a first connector and a second connector selectively attachable thereto, a first housing holding the processor, the network interface, the user interface, and the first connector, and a second housing separate from the first housing holding the biosensor and the second connector, so that the processor receives the signal from the biosensor via the first and second connectors when the first and second connectors are attached together; or the network interface comprising a cellular interface and the user interface comprising a touchscreen.

In other examples, the physiological measurement can include the storage device being configured to store respective credentials of the user on a plurality of social networks, so that the processor transmits the analyte data and the stored respective credential to each of the plurality of social networks, and awaits the response data from any of the plurality of social networks; the processor configured to receive from the social network an identifier corresponding to the transmission, delay a selected length of time, and transmit a query including the identifier to the social network to determine whether the response data is available for retrieval; the processor configured to receive supplemental data corresponding to the signal via the user interface and transmit the supplemental data to the social network with the analyte data; the network interface comprising a cellular interface and the system further including a touchscreen, a first connector and a second connector selectively attachable thereto, a first housing holding the processor, the network interface, the user interface, and the first connector, and a second housing separate from the first housing holding the biosensor and the second connector, so that the processor receives the signal from the biosensor via the first and second connectors when the first and second connectors are attached together; or a mechanical alerting device, so that the processor provides an alert via the mechanical alerting device when the response data is retrieved.

In other examples, methods for processing analyte data can include transmitting to a second social network a query for analyte-data-request records, receiving from the second social network an indication of an analyte-data-request record, retrieving second credentials of the user from the storage device, the second credentials corresponding to the second social network, and, in response to the received indication from the second social network, transmitting the second credentials and the stored analyte data to the second social network; receiving supplemental data (e.g., including meal data corresponding to the analyte data) and automatically transmitting the supplemental data with the stored analyte data to the social network; receiving the supplemental data by automatically querying the user for the supplemental data via a user interface; after transmitting the credentials and the stored analyte data, receiving a corresponding identifier, retrieving response data corresponding to the received identifier from the social network, wherein the response data correspond to a second user different from the user, and presenting an indication of the response data; waiting a selected time after receiving the identifier and before retrieving the response data; or automatically storing the retrieved response data and presenting the indication by receiving a user command to display response data and, in response to the user command, displaying at least some of the stored response data on a display.

In the aforementioned aspects of the disclosure, the steps of receiving, storing, transmitting, receiving, retrieving, or transmitting (possibly in conjunction with an equation) may be performed be an electronic circuit or a processor. These steps may also be implemented as executable instructions stored on a computer readable medium; the instructions, when executed by a computer may perform the steps of any one of the aforementioned methods.

In additional aspects of the disclosure, there are computer readable media, each medium comprising executable instructions, which, when executed by a computer, perform the steps of any one of the aforementioned methods.

In additional aspects of the disclosure, there are devices, such as test meters or analyte testing devices, each device or meter comprising an electronic circuit or processor configured to perform the steps of any one of the aforementioned methods.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

MODES FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention or the attached claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" are used interchangeably. These terms can refer to any can refer to a patient using a glucose measuring device or another person (e.g., a parent or guardian, nursing staff member, home care employee, or other caretaker) or animal subject and are not intended to limit the systems or methods to human use, although use of the subject invention in a human patient represents a preferred embodiment. As used herein, "oscillating signal" includes voltage signal(s) or current signal(s) that, respectively, change polarity or alternate direction of current or are multi-directional. Also used herein, the phrase "electrical signal" or "signal" is intended to include direct current signal, alternating signal or any signal within the electromagnetic spectrum. The terms "processor"; "microprocessor"; or "microcontroller" are intended to have the same meaning and are intended to be used interchangeably. As used herein, the term "annunciated" and variations on its root term indicate that an announcement may be provided via text, audio, visual or a combination of all modes or mediums of communication to a user. The term "drug" may include hormones, biologically active materials, pharmaceuticals or other chemicals that cause a biological response (e.g., a glycemic response) in the body of a user.

Throughout this disclosure, exemplary physiological parameters such as for example analyte levels in the form of blood glucose levels are given in mg/dL. These levels can be divided by 18 to obtain mmol/L. Intervals or other numerical ranges are denoted using parentheses for open endpoints (the value of the endpoint is not included in the interval) and square brackets for closed endpoints (the value of the endpoint is included in the interval), as is common in the mathematical art.

Figure 1:
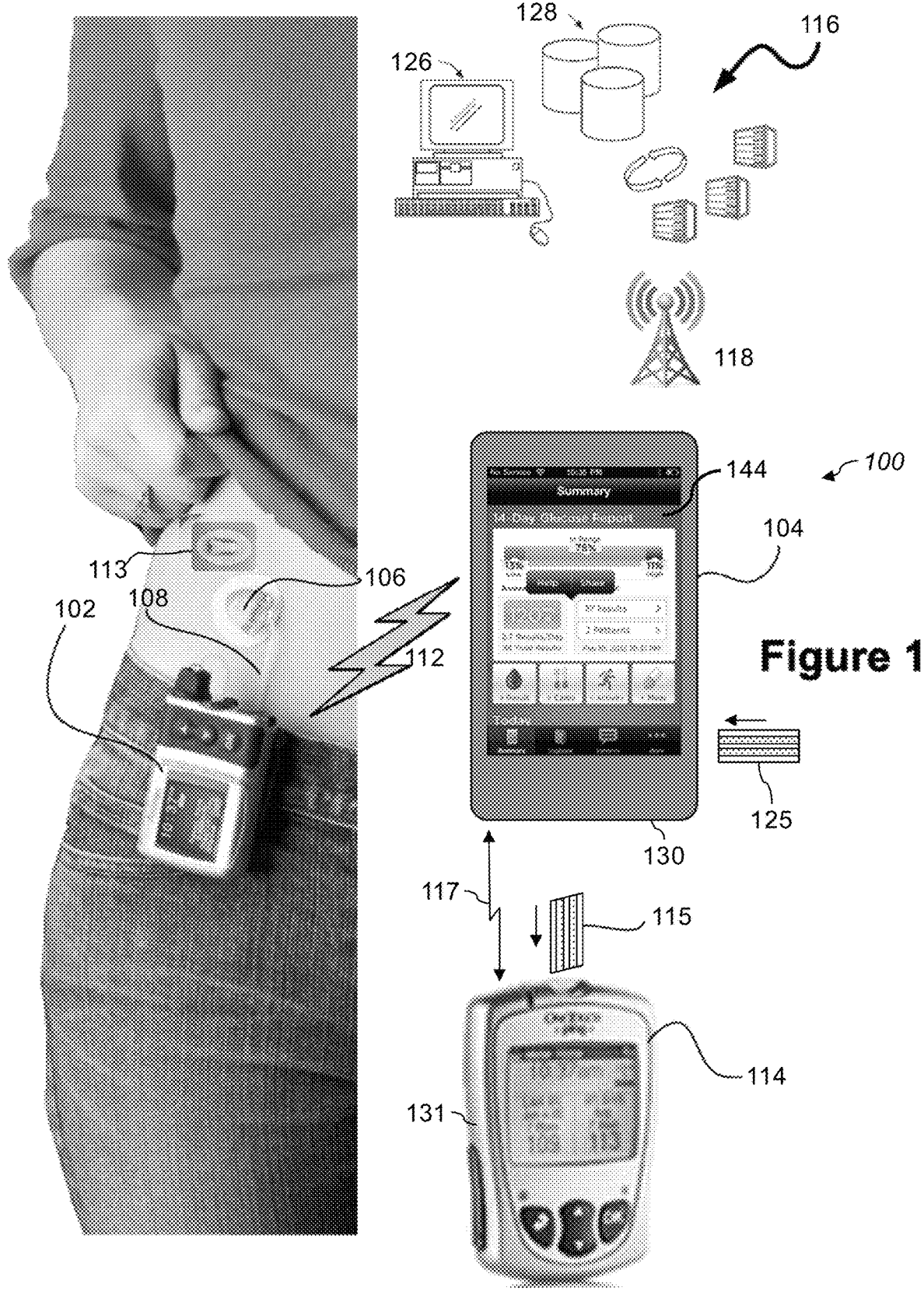
FIG. 1 illustrates an exemplary glucose management system and related components.

FIG. 1 illustrates a physiological measurement system 100 and related components according to an exemplary embodiment. The physiological measurement 100 can also include devices for performing glucose management, as described below. The physiological measurement 100 includes a drug delivery device 102 and a controller 104. The drug delivery device 102 is connected to an infusion set 106 via flexible tubing 108. Various embodiments of the invention can also be used with injections via syringe or insulin pen instead of or in addition to infusion via the drug delivery device 102. The controller 104 can include a touchscreen 144 with which the user interacts.

The drug delivery device 102 is configured to transmit and receive data to and from the controller 104 via, for example, a radio frequency (RF) communications link 112. The drug delivery device 102 may also function as a stand-alone device with its own built in controller. In one embodiment, the drug delivery device 102 is an insulin infusion device and the controller 104 is a hand-held portable controller. In such an embodiment, data transmitted from the drug delivery device 102 to the controller 104 may include information such as, for example, insulin delivery data, blood glucose information, basal, bolus, insulin to carbohydrates ratio or insulin sensitivity factor. Data transmitted from the controller 104 to the drug delivery device 102 can include glucose test results and a food database to allow the drug delivery device 102 to calculate the amount of insulin to be delivered by the drug delivery device 102. Alternatively, the controller 104 may perform basal dosing or bolus calculation and send the results of such calculations to the drug delivery device. A glucose meter 114 (here, an episodic meter) provides data to either or both of the controller 104 and the drug delivery device 102. The glucose meter 114 can provide data to the controller 104 via a wired or other physical connection, e.g., via connectors 328, 329, FIG. 3, or via a wireless connection such as a radio frequency (RF) communications link 117. The RF communications link 117 can include, e.g., a BLUETOOTH, BLUETOOTH Low Energy (BLE), near-field communications (NFC), or ZIGBEE wireless connection. The glucose meter 114 can measure a fluid sample placed on a test strip 115. The two hatched areas on the test strip 115 graphically represent two electrodes, as is discussed below with reference to FIG. 2.

In various embodiments, the controller 104 is combined with the glucose meter 114 into an integrated monolithic device having a housing 130. This can be represented, for example, by a test strip 125. In other embodiments, the controller 104 and the glucose meter 114 are two separable devices that are dockable with each other to form an integrated device. Each of the devices 102, 104, and 114 has a suitable micro-controller (not shown for brevity), which is programmed to carry out various functionalities. Examples of micro-controllers that can be used are discussed below with reference to a processor 386, FIG. 3.

The drug delivery device 102 or the controller 104 can be configured for bi-directional communication with a social network 116 through, for example, a wireless communication network 118, and/or a wired communications network such as a telephone or Ethernet connection. The social network 116 can be a Web site or other electronic community primarily focused on diabetes, e.g., diabetes.co.uk. The social network 116 can also be a general-interest electronic community, such as FACEBOOK or TWITTER, through which people can interact about diabetes. For example, the NY Diabetes Support Group in New York, N.Y., has a FACEBOOK page. The social network 116 can include one or more server(s) 126 or storage device(s) 128.

The drug delivery device 102 can include electronic signal processing components including a central processing unit and memory elements for storing control programs and operation data, a radio frequency module (not shown) for sending and receiving communication signals (e.g., messages) to and from the controller 104, a display for providing operational information to the user, a plurality of navigational buttons for the user to input information, a battery for providing power to the system, an alarm (e.g., visual, auditory or tactile) for providing feedback to the user, a vibrator for providing feedback to the user, a drug delivery mechanism (e.g., a drug pump and drive mechanism) for forcing a insulin from a insulin reservoir (e.g., a insulin cartridge) through a side port connected via the flexible tubing 108 to an infusion set 106 and into the body of the user.

Glucose levels or concentrations in physiological fluid (e.g., blood, saliva, or interstitial fluid) of a subject can be determined by the use of appropriate monitors. The glucose meter 114 utilizes electrochemical sensor technology to measure glucose with two or more electrodes operably connected to the sensor electronics.

Figure 2:
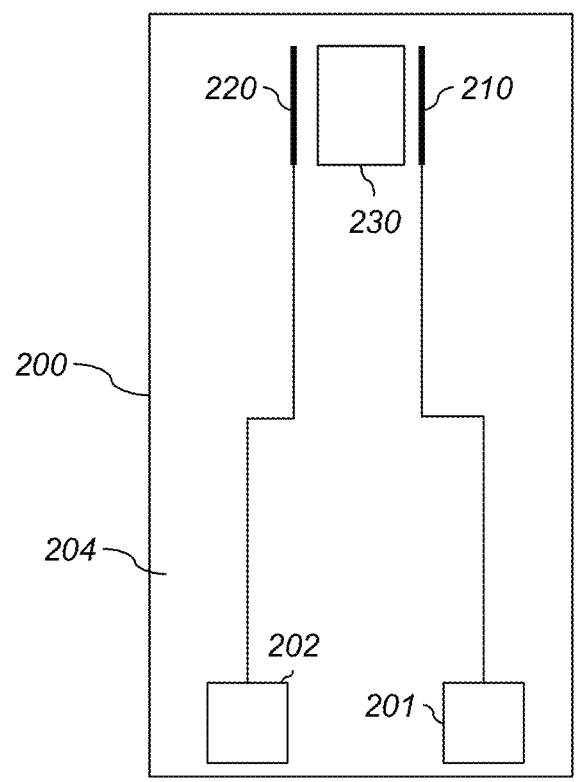
FIG. 2 shows an exemplary test strip for use in an episodic glucose meter.

FIG. 2 shows an exemplary test strip 200 for use in an episodic glucose meter. The test strip 200 is defined by a planar substrate 204 that supports a pair of contact pads 201, 202 at one end of the strip and a pair of electrodes 210, 220. One of the electrodes 220 is a working electrode formed by sputtering a Pd coating onto a polyester base forming the substrate 204. A dry reagent layer is used and includes buffer, mediator, and enzyme, as described herein. The remaining electrode 210 is a reference electrode formed by sputtering an Au coating on the substrate 204. The contact pads 201, 202 connect to the electrodes 210, 220, respectively, and permit applying or detecting electrical signals across a sample-receiving chamber 230 between the electrodes 210, 220. The sample-receiving chamber 230 can have a volume ranging from, e.g., about 0.1 microliters to about 5 microliters. Various enzymes in the sample-receiving chamber 230 can assist in transducing the analyte (e.g., glucose) in the fluid sample (e.g., blood) into a current, potential, or other quantity that can be measured electrically. Exemplary enzymes include glucose oxidase, glucose dehydrogenase (GDH) based on a pyrroloquinoline quinone co-factor, and GDH based on a nicotinamide adenine dinucleotide co-factor.

In use, top ends of the electrodes 210, 220 are in contact with an electrolyte phase (not shown), which is a free-flowing fluid phase disposed between the electrodes 210, 220. An enzyme, e.g., glucose oxidase, can cover the electrolyte phase. The electrode 210 can be a working electrode and the electrode 220 can be a counter electrode. In an example using glucose oxidase, a current is produced at the working electrode (and flows through the circuitry to the counter electrode). That current is representative of the concentration of glucose in the subject's body. The glucose meter 114 can measure the current through the electrodes 210, 220 to determine the analyte level of the fluid sample in the sample-receiving chamber 230. Exemplary glucose sensors and associated components are shown and described in U.S. Pat. Nos. 6,179,979, 8,163,162, and 6,444,115, which are incorporated by reference herein in their entireties.

Continuous glucose monitors (CGMs) 113 can also be used as biosensors that are attached directly to the skin of the user, e.g., as described in U.S. Pat. No. 7,276,029, incorporated by reference herein. An exemplary CGM sensor 113 uses amperometric electrochemical sensor technology to measure an analyte. The CGM sensor includes three electrodes operably connected to the sensor electronics and covered by a sensing membrane and a biointerface membrane, which are attached by a clip. The top ends of the electrodes are in contact with an electrolyte phase, which is a free-flowing fluid phase disposed between the sensing membrane and the electrodes. The sensing membrane may include an enzyme, e.g., analyte oxidase, which covers the electrolyte phase. The $H_2O_2$ produced from the analyte oxidase reaction further reacts at the surface of working electrode and produces two protons (2H+), two electrons (2e−), and one oxygen molecule ($O_2$). A potentiostat is used to measure the electrochemical reaction(s) at the electrode(s) by applying a constant potential between the working and reference electrodes to produce a current value. The current that is produced at the working electrode (and flows through the circuitry to the counter electrode) is proportional to the diffusional flux of $H_2O_2$. Accordingly, a raw signal may be produced that is representative of the concentration of analyte in the user's body, and therefore may be utilized to estimate a meaningful analyte value. A CGM sensor 113 can measure analyte levels in, e.g., interstitial fluid and provide real-time analyte levels every 5-10 minutes to the controller 104 via a wireless transmission.

Various glucose management systems may include an episodic biosensor and an infusion pump. An example of such a system is OneTouch Ping® Glucose Management System manufactured by the Animas Corporation. The "ezBG" feature of this system computes an amount of insulin to be delivered by the infusion pump using the results of an episodic glucose measurement. In various embodiments, the CGM sensor 113 may also be utilized in conjunction with the episodic biosensor 115 and the social-network communications are used with components similar to the components of such a system.

Figure 3:
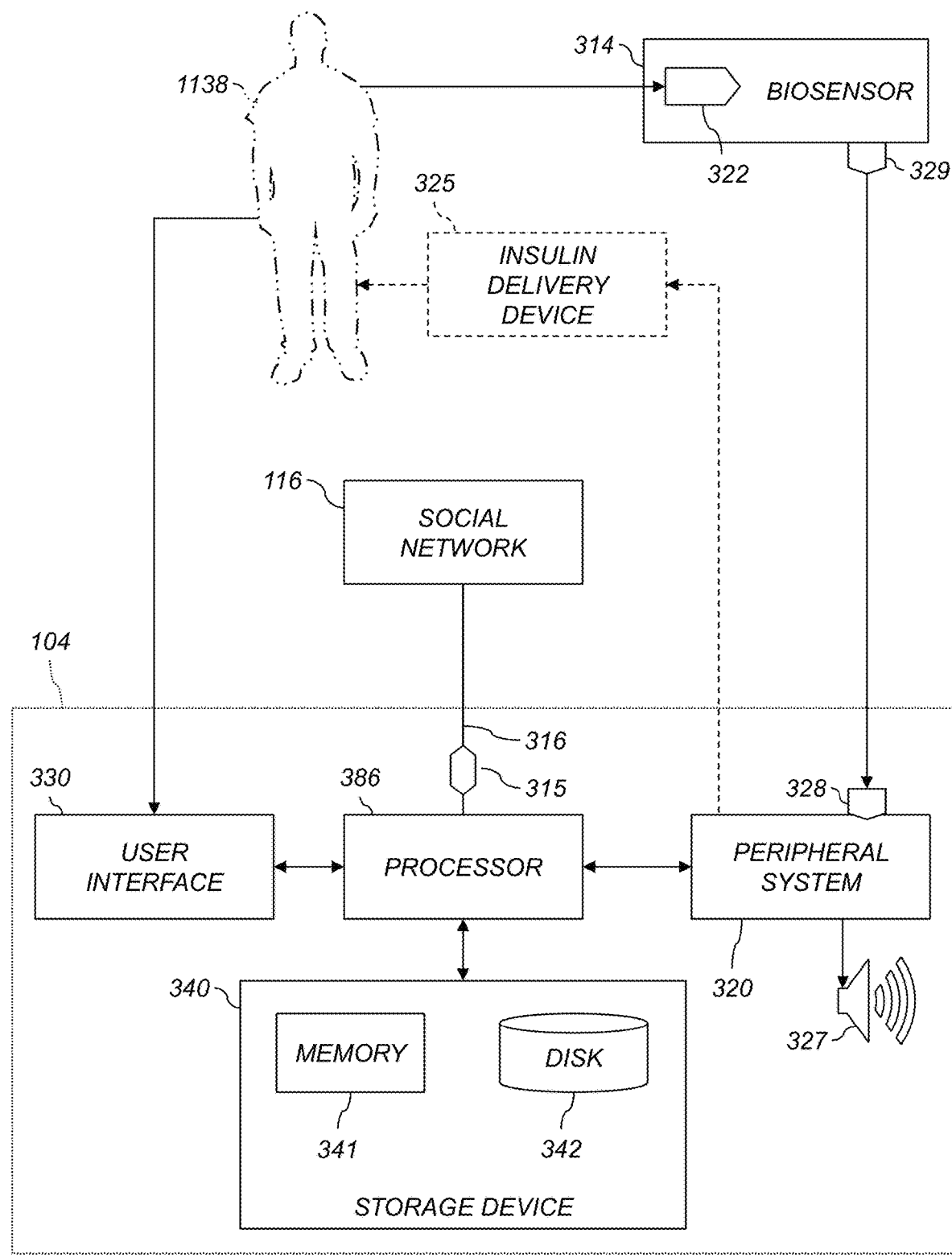
FIG. 3 shows an exemplary system for the management of blood glucose.

FIG. 3 shows an exemplary system for the measurement or management of blood glucose, including data-processing components for analyzing data and performing other analyses and functions described herein, and related components. A subject 1138, e.g., a patient or user of the system, and the social network 116, are not part of the system but are shown for purposes of context. The controller 104 communicates with a biosensor 314 and with the social network 116.

A biosensor 314, e.g., an episodic glucose meter system or CGM, is adapted to measure respective glucose levels of the subject 1138 at discrete time intervals, e.g., continually or intermittently, and provide respective glucose measurement data indicating each measured glucose level. The biosensor 314 can include one or more glucose sensor(s) 322, e.g., a test strip 200, FIG. 2 or the CGM sensor 113. In various embodiments, the processor 386 is connected to the biosensor 314 and configured to receive the signal from the biosensor 314 and automatically determine analyte data using the signal.

An insulin delivery device 325 can be a pump configured to deliver insulin in response to a delivery control signal from the processor 386. The processor 386 can determine the delivery control signal using analyte data from the biosensor 314. For example, the processor 386 can run a control law such as a proportional-integral-derivative (PID) control law or a model-predictive control law (MPC) that takes the sensed analyte level from the biosensor 314 as input and produces an insulin-delivery amount as output. The insulin delivery device 325 can then deliver a corresponding amount of insulin, e.g., to the subject 1138. The insulin delivery device 325 can also be a pen with which insulin is manually injected into the subject.

The controller 104 includes the processor 386 that receives glucose measurement data from the biosensor 314 and can command the insulin delivery device 325 (if present) to deliver insulin. The controller 104 can also include a peripheral system 320, a user interface 330, and a storage device 340 communicatively connected to the processor 386. The processor 386 can be communicatively connected to the social network 116, e.g., a Web site such as FACE-BOOK or diabetes.co.uk, via the Internet or an X.25 or other network, as discussed below.

The processor 386 includes one or more data processor(s) that implement processes of various embodiments described herein. A "data processor" is a device for processing data and can include a central processing unit (CPU) or other microprocessor, a microcontroller, a field-programmable gate array (FPGA), a programmable logic device (PLD), a programmable logic array (PLA or PAL), or any other device configured for processing, managing, or handling data as described herein, whether implemented with electrical, magnetic, optical, biological components, or otherwise.

The phrase "communicatively connected" includes any type of connection, wired or wireless, between devices, data processors, or programs in which data can be communicated. Subsystems such as the peripheral system 320, the user interface 330, and the storage device 340 are shown separately from the processor 386 but can be stored completely or partially within the processor 386.

The storage device 340 includes or is communicatively connected with one or more tangible non-transitory computer-readable storage medium(s) configured to store information, including the information needed to execute processes according to various embodiments. A "tangible non-transitory computer-readable storage medium" as used herein refers to any non-transitory device or article of manufacture that participates in storing instructions which may be provided to the processor 386 for execution. Such a non-transitory medium can be non-volatile or volatile. Examples of non-volatile media include floppy disks, flexible disks, or other portable computer diskettes, hard disks, magnetic tape or other magnetic media, Compact Discs and compact-disc read-only memory (CD-ROM), DVDs, BLU-RAY disks, HD-DVD disks, other optical storage media, Flash memories, read-only memories (ROM), and erasable programmable read-only memories (EPROM or EEPROM). Examples of volatile media include dynamic memory, such as registers and random access memories (RAM). Storage media can store data electronically, magnetically, optically, chemically, mechanically, or otherwise, and can include electronic, magnetic, optical, electromagnetic, infrared, or semiconductor components.

Embodiments of the present invention can take the form of a computer program product embodied in one or more tangible non-transitory computer readable medium(s) having computer readable program code embodied thereon. Such medium(s) can be manufactured as is conventional for such articles, e.g., by pressing a CD-ROM. The program embodied in the medium(s) includes computer program instructions that can direct the processor 386 to perform a particular series of operational steps when loaded, thereby implementing functions or acts specified herein.

In an example, the storage device 340 includes a memory 341, e.g., a random-access memory, and a disk 342, e.g., a tangible computer-readable storage device such as a hard drive or a solid-state flash drive. Computer program instructions are read into the memory 341 from the disk 342, or a wireless, wired, optical fiber, or other connection. The processor 386 then executes one or more sequences of the computer program instructions loaded into the memory 341, as a result performing process steps and other processing described herein. In this way, the processor 386 carries out a computer implemented process that provides for technical effects of converting glucose to analyte data and communicating that data. For example, blocks of the flowchart illustrations or block diagrams herein, and combinations of those, can be implemented by computer program instructions. The memory 341 can also store data used by running programs. In an example, the memory 341 (or other components in the storage device 340) stores transmission identifiers such as Message-IDs, as is discussed below.

Program code to carry out methods described herein can execute entirely on a single processor 386 or on multiple communicatively-connected processors 386. For example, code can execute wholly or partly on a user's computer and wholly or partly on a remote computer, e.g., a server. The remote computer can be connected to the user's computer through a network. The user's computer or the remote computer can be non-portable computers, such as conventional desktop personal computers (PCs), or can be portable computers such as tablets, cellular telephones, smartphones, or laptops.

The peripheral system 320 can include one or more devices configured to provide digital content records or other data to the processor 386. In this example, the biosensor 314 (with glucose sensor(s) 322) and the insulin delivery device 325 are connected to the processor 386 via the peripheral system 320. The biosensor 314 and the insulin delivery device 325 can also be directly connected to the processor 386. The peripheral system 320 can also include digital still cameras, digital video cameras, cellular phones, or other data processors. The peripheral system 320 can also include one or more bus bridge(s), e.g., to operatively connect devices having USB, FIREWIRE, RS-232, or other interfaces to processor 386. The processor 386, upon receipt of data from a device in the peripheral system 320, can store that data in the storage device 340.

The user interface 330 can include a mouse, a keyboard, another computer (connected, e.g., via a network or a null-modem cable), a microphone and speech processor or other device(s) for receiving voice commands, a camera and image processor or other device(s) for receiving visual commands, e.g., gestures, one or more touch sensor(s), button(s), switch(es), or any other device or combination of devices from which data is input to the processor 386. In this regard, although the peripheral system 320 is shown separately from the user interface 330, the peripheral system 320 can be included as part of the user interface 330. In at least one embodiment, the user interface 330 can be operated by the subject 1138.

The user interface 330 also can include a display device, a processor-accessible memory, or any device or combination of devices to which data is output by the processor 386. In this regard, if the user interface 330 includes a processor-accessible memory, such memory can be part of the storage device 340 even though the user interface 330 and the storage device 340 are shown separately in FIG. 3.

In various embodiments, a network interface 315 is coupled via a communications link 316 to the social network 116. The network interface 315 is configured to selectively convey data bidirectionally between the processor 386 and the social network 116 via the communications link 316. For example, the network interface 315 can be an integrated services digital network (ISDN) card or a modem to provide a data communication connection to a corresponding type of telephone line. As another example, the network interface 315 can be a network card to provide a data communication connection to a compatible local-area network (LAN), e.g., an Ethernet LAN, or wide-area network (WAN). Wireless links, e.g., WiFi or GSM, can also be used. The network interface 315 sends and receives electrical, electromagnetic or optical signals that carry digital data streams representing various types of information across the communications link 316 to the social network 116 or other networks or network-attached devices. The communications link 316 can be connected to the social network 116 via a switch, gateway, hub, router, or other networking device.

The processor 386 can send messages and receive data, including program code, to and from the social network 116 via the communications link 316 and the network interface 315. For example, a server in the social network 116 can store requested code for an application program (e.g., a JAVA applet or JAVASCRIPT script) on a tangible non-volatile computer-readable storage medium to which it is connected. The server can retrieve the code from the medium and transmit it through the Internet, thence a local ISP, thence a local network, thence the network interface 315. The received code can be executed by processor 386 as it is received, or stored in storage device 340 for later execution.

Users sometimes desire to respond to Analyte-data requests presented in electronic communities such as the social network 116. To permit more readily responding to these responses, the processor 386 determines a physiological parameter in the form of an analyte concentration using the signals received from the biosensor 314. The processor 386 then transmits a query for analyte-data-request records to the social network 116.

An exemplary analyte-data-request record is a forum post on a diabetes-support Web site with the subject "What's your ANALYTE (e.g., BLOOD GLUCOSE)?" The term "analyte-data-request record," as used herein, refers to a content record stored by the social network 116 soliciting analyte (e.g., blood glucose) information, whether specific values or trend information (e.g., a forum post titled "How well are you keeping your ANALYTE (E.G., BLOOD GLUCOSE) in range?"). Analyte-data-request records are often produced by humans interacting with the social network 116. However, analyte-data-request records can also be produced programmatically. For example, the social network 116 can produce a new analyte-data-request record every n hours, e.g., daily (n=24) or twice-daily (n=12). Analyte-data-request records can be included in forum posts, blog posts, news stories, Web site banners or sidebars, or other content records.

Analyte-data-request records can be identified by the social network 116 by full text searching of the titles or bodies of content records on the social network 116. Analyte-data-request records can also be identified by tags or other information provided at the time a content record is created. For example, the social network 116 can provide an input form (e.g., a <form> element in a Hypertext Markup Language, HTML, document) that permits a user of the social network 116 to provide a new forum post. The input form can include a checkbox, drop-down list, or other input control that permits the user to indicate whether the new forum post is an analyte-data-request record. If the new forum post is an analyte-data-request record, a flag is set in the forum post so the social network 116 can readily identify the forum post as an analyte-data-request record. In another example, any post from a designated account (e.g., user "analyte-check") can be automatically regarded as an analyte-data-request record. Such posts can be, e.g., microblogging messages from the designated account ("@analyte-check").

The query transmitted by the processor 386 can be, e.g., a Hypertext Transfer Protocol (HTTP) GET request for a search URL, with a query string specifying that the desired search results are analyte-data-request records. Exemplary query criteria are "posts tagged as analyte-data-request records" or "posts with 'Analyte level' (e.g., blood glucose level)?' in the subject." The processor 386 transmits the query to the social network 116. The processor 386, via fields set in the query, can specify limits on the records to be returned, e.g., only "today's posts" (records created on the date the query is transmitted). The social network 116 can also set limits, e.g., by not searching posts older than a certain date or posts larger than a certain size.

Query criteria can be expressed in various forms and can be specified in a form the social network 116 will be able to parse and understand. Different query strings or query-string formats can be used for different social networks. For example, an HTTP GET request can include a query string beginning with a question mark "?" followed by one or more name=value pairs separated by ampersands ("&"). In another example, a Structured Query Language (SQL) query string can include a "SELECT" command with a "WHERE" clause listing the criteria. HTTP and SQL queries are well known in the art. Other query formats can also be used.

In an example, a query includes various criteria that are specific the monitored analyte. In the examples for glucose monitoring, the query requests case-insensitive, whitespace-insensitive, automatically-stemmed, full-text search of all records, e.g., all blog posts, USENET or other newsgroup or forum posts, or FACEBOOK updates, that were posted less than 24 hours ago. Results, i.e., records determined to be analyte-data-request records, should include a phrase indicating a time of day, e.g., "morning," "afternoon," "evening," "after breakfast" (or "after" followed by the noun describing any other meal), or "today." The word "blood" (or the stemmed form "bloods") should occur in results in proximity to one of the words "sugar," "glucose," or "level" (or stemmed forms of those, e.g., "levels"), and another item. The other item can be a second-person pronoun (e.g., "you" or "your"), a phrase relating to sugar (e.g., "how sweet"), or a number. e.g., matching the regular expression [0-9]+(\.[0-9]*){,1}

Users of the social network 116 can be literate in one or more natural language(s). Accordingly, any query involving text can be presented in one or more language(s). The processor 386 can be pre-programmed with a selection of language(s) to use, or can retrieve such a selection from the storage device 340 or via the user interface 330. The user can select language(s), e.g., on a user-settings screen of the controller 104. In an example, if English and German are selected, the query can request records with either "blood glucose" or "Blutzucker" in the full text of the record. Tags associated with records, and usernames, handles, or other user identifiers, can include user-provided text, so those fields can be searched in the selected language(s) also.

The processor 386 can also specify in the query that the returned records be limited to those in one or more selected language(s). In an example, the social network 116 includes users literate in multiple languages, e.g., English and Scottish Gaelic. The query can include one or more ISO 639-1 language codes (or other language identifiers, and likewise throughout), e.g., "requestlang=gd" to request only Scottish Gaelic analyte-data-request records, or "requestlang=gd,en" to request Scottish Gaelic or English request records. While the exemplary embodiment of the physiological parameter is specific to blood glucose monitoring, one skilled in the art would also be able to apply the principles of the invention for other analytes (e.g., ketones, cholesterol) or to other physiological parameters such as, for example, heart rhythm, blood pressure, brain waves, galvanic skin response, oxygen saturation levels, heart pulses, or combinations of the physiological parameters.

Here and throughout this disclosure, "literacy," "text," and similar terms used with reference to the social network 116 and data transmitted thereto or received therefrom also refer to data transmitted to or from an illiterate user via, e.g., text-to-speech and speech-synthesis engines. The term "literacy" is also intended herein to include the ability to communicate using Braille or other tactile code systems, e.g., for visually-impaired users.

In various embodiments, the processor 386 is configured to receive query control data, store the query control data in the storage device 340, and prepare the query string using the query control data. The processor 386 can receive the query control data, e.g., from the user via the user interface 330 or from an external device via the peripheral system 320. The query control data can include, e.g., one or more word(s) or search phrase(s) to be included in the query criteria, either as optional or as required. In an example, the query control data can specify that "sugar" or "glucose" can be used interchangeably. The processor 386 then prepares the query string, in part, by replacing every instance of "sugar" in the query string with "(sugar|glucose)" ("|" being the OR operator in regular expressions).

If one or more analyte-data-request records are present, the social network 116 can respond to the query with an indication of an analyte-data-request record. The processor 386 receives this indication from the social network 116. The processor 386 then transmits the determined analyte data to the social network 116 in response to the indication. The social network 116 can then produce a content record, e.g., a response post, including the determined analyte data. Hence, as part of applicants' inventive concept or technical contribution to the art, the user of the controller 104 derives the benefit of interacting with the social network 116 without being required to manually locate analyte-request records and transcribe analyte data into a response post.

The content record can various fields, e.g., Handle (username), Timestamp (e.g., date and time of posting), To, From, CC, Subject, Body, Tags, Image, Avatar, In-Reply-To, User-Agent, Importance, Text before the jump break, or Text after the jump break. The "jump break" is a marker commonly used in blogging systems so that text before the jump break is displayed with a "read more" link the user can click to see the text after the jump break. The processor 386 can transmit values for some or all of these fields to the social network 116 with the determined analyte data, and the social network 116 can incorporate the data from the processor 386 into the produced content record. The social network 116 can transform or ignore some of the data provided by the processor 386. For example, the social network 116 can ignore any specification by the processor 386 of a Timestamp value, instead assigning the actual date and time of receipt of the data as the Timestamp. The social network 116 can also, e.g., resize any image data provided in an Image or Avatar field.

The processor 386 can provide data for the fields of the content record based on various sources. In various embodiments, the processor 386 retrieves data for one or more of the fields from the storage device 340. For example, the processor 386 can provide a User-Agent field retrieved from the storage device 340, e.g., a ROM programmed with a string identifying the controller 104. An exemplary User-Agent field is "Mozilla/5.0 (Windows NT 6.1; rv:21.0) Gecko/20100101 Firefox/21.0" for the MOZILLA FIREFOX Web browser, version 21. In another example, the processor 386 can receive data for one of the fields, e.g., the Avatar field, via the user interface 330 and store the received data in the storage device 340. The processor 386 can then retrieve the stored data and transmit it with the determined analyte data. This permits users to influence the data in the produced content records, e.g., by specifying a desired Avatar, Handle, or Subject.

In various embodiments, the processor 386 produces data for one or more of the fields by retrieving a template from the storage device 340 and processing the template. The template can be stored in the storage device 340 at the time of manufacturing (e.g., a manufacturer's default), by a healthcare provider (HCP), or by the user. An exemplary template for the Subject field is "My BG is {bg}". In this example, curly braces delimit "active strings" that are interpreted by the processor 386. The processor 386 is configured to retrieve the template from the storage device 340 and to replace all instances of the active string "{bg}" in the template with the determined analyte data. In this way, the content record provided by the social network 116, including the provided Subject data from the processor 386, will include a Subject of, e.g., "My BG is 110".

Another exemplary template is:

"My BG is {bg} { ':)' if 70<=bg<=150 else ':(' }".

The processor 386 interprets "{bg}" as described above. The processor interprets the active string "{ ':)' if 70<=bg<=150 else ':(' }" by comparing the determined analyte data to 70 mg/dL and 150 mg/dL. If the determined analyte data are on the interval [70,150], the processor 386 replaces the active string with ":)" (a happy-face emoticon), since [70,150] is an exemplary range of normal blood glucose. If the determined analyte data are outside [70,150], the processor 386 replaces the active string with ":(" (a sad-face emoticon). In this way, the processor 386 produces Subject fields such as "My BG is 100 :)" and "My BG is 200 :(". The emoticon can permit other users of the social network 116 to readily determine whether the determined analyte data are indicative of in-control blood glucose. Exemplary systems for interpreting templates include APACHE Velocity, DJANGO, JAVA Server Pages, PHP, and SMARTY.

Templates can also be used in non-text fields. For example, the processor 386 can transmit a number to be included in an Importance field of the content record. The value 0 denotes a normal message, in this example, and the value 1 denotes a message to be flagged as "important," e.g., by placing an exclamation-mark icon next to the message when displayed. The processor 386 can produce the Importance number by interpreting the template {integer(bg<60)} to produce a 1 (a true logic value) if the most recent BG reading is less than 60 mg/dL, and a 0 (a false logic value) if the most recent BG reading is at least 60 mg/dL.

In various embodiments, the processor 386 is configured to retrieve field values or produce field values by interpreting templates, in any combination. The processor 386 can then present via the user interface 330 the field values to be transmitted with the determined analyte data. The processor 386 can receive, via the user interface 330, modifications to one or more of the presented field values. This permits the user to readily post to the social network 116 by simply accepting the presented values, or to customize the field values that will influence a particular content record. In various embodiments, the processor 330 is configured to automatically transmit the presented field values a selected time after presenting them, e.g., five minutes, if the user does not interact with the user interface 330 in that time.

In various embodiments, the storage device 340 stores user credentials (e.g., a username and password, or an authentication token such as an OAuth token). The processor 386 retrieves the user credentials from the storage device 340 and transmits them to the social network 116 in association with the transmission of the determined analyte data. This permits the social network 116 to associate the user's identity with the determined analyte data. The processor 386 can also transmit the user credentials with the query if the social network 116 provides access to content records only to authorized users.

In various embodiments, the storage device 340 stores respective user credentials for a plurality of social networks (e.g., FACEBOOK and TWITTER). The processor 386 presents a menu of the plurality of social networks to the user of the system (e.g., the subject 1138) via the user interface 330. The processor receives a selection of one of the plurality of social networks via the user interface 330, retrieves the user credentials corresponding to the selection from the storage device, and transmits the retrieved user credentials with the determined analyte data or with the query. This permits the user to select a desired social network while maintaining the reduced user burden of locating requests and posting responses. In other embodiments, the processor automatically sends queries to multiple social networks using the respective stored user credentials. The queries can be sent simultaneously or time-staggered (e.g., sending a query to a different network every 2 hours, the sequence of networks being fixed or, e.g., randomly-chosen). The processor receives indications from and transmits analyte data to each of the social networks. In various embodiments, the processor 386 is adapted to receive from the user a selection of social networks. The processor 386 can delete credentials for the selected social networks from the storage device 340, if credentials have been stored. The processor 386 can also store an indication of the selected social networks (a "blacklist"). When the processor 386 receives credentials from the user, the processor 386 can then store those credentials in the storage device 340 only if the social network for those credentials is not indicated in the stored blacklist. These embodiments provide the user additional control over which social networks are to be accessed.

In various embodiments, the storage device 340 can store indications of one or more social networks that should always be selected. The storage device 340 can also stored indications of one or more social networks that should not be selected. The processor 386 retrieves the indications from the storage device 340, and can present some or all of the retrieved indications via the user interface 330. When a selection of one or more of the plurality of social networks is received via the user interface 330, the processor 386 adds to the selection any indicated social networks that should always be selected, and removes from the selection any indicated social networks that should not be selected. The processor 386 then transmits credentials with analyte data or with a query, as described above.

For example, the processor 386 can receive the selection by soliciting a uniform resource locator (URL) of a social-networking Web site via the user interface 330. Indications of social networks that should not be selected can include URLs of Web sites, and the received URL can be compared against the URLs indicated. This can protect the controller 104, e.g., from Web sites or other social networks that are known to host viruses or other malicious code. Indications of social networks that should always be selected can be programmed into the storage device 340 by a health care provider (HCP) so that, e.g., a social network operated by the HCP always receives updated information about the user's BG. This can provide the HCP with frequently-updated data regarding the user's health.

In various aspects, the housing 130, FIG. 1, holds the biosensor 314, the processor 386, the network interface 315, and the user interface 330. For example, the housing 130, FIG. 1, can be, e.g., a housing of a fully-integrated analyte (e.g., blood glucose) meter with social-network communications capability. This advantageously permits the user to read blood glucose and conduct interactions regarding blood glucose using only a single device. The user interface 330 can include a display and the processor 386 can display content records retrieved from the social network 116 on the display.

In various embodiments, a first housing 130, FIG. 1, holds the processor 386, the network interface 315, the user interface 330, and a first connector 328. A second housing 131, FIG. 1, separate from the first housing 130 can retain the biosensor 314 and a second connector 329. The second connector 329 is selectively attachable to the first connector 328. The processor 386 receives the signal from the biosensor 314 via the first and second connectors 328, 329 when the first and second connectors 328, 329 are attached together. In an example, the first housing 130 is a smart-phone housing. The network interface 315 includes a cellular interface and the user interface 330 includes a touchscreen. The second housing 131 can be a housing of a glucose-monitor device adapted to connect to a smartphone, e.g., an IBGSTAR glucose meter that attaches to an APPLE IPHONE. Smartphones employing various operating systems can be used. APPLE IOS, GOOGLE ANDROID, BLACKBERRY OS, WEBOS, MICROSOFT WINDOWS PHONE, and other operating systems can be used.

In an example of selectively-attachable connectors, the first connector 328 can include a female jack such as a 0.100" dual-row receptacle and the second connector 329 can include a corresponding 0.100" dual-row pin header. Exemplary connectors are the AMPMODU series from TE CONNECTIVITY. In another example, the first connector 328 is a docking receptacle such as a JAE DD1R030HA1R1300 30-pin, 0.5 mm receptacle, and the second connector 329 is a corresponding plug such as a JAE DD1P030MA1. These JAE connectors are similar to those used in personal media players such as the APPLE IPOD. In yet another example, one of the first connector 328 and the second connector 329 is a pad array and the other of the first connector 328 and the second connector 329 is a corresponding array of pogo pins. In any of these examples, mating features on the first connector 328 and the second connector 329 or mechanical latches or facing pairs of magnets on the first housing 130 and the second housing 131 can be used to hold the first housing 130 and the second housing 131 together.

In many diabetes-support electronic communities such as the social network 116, users can provide content records (e.g., forum posts) and other users can respond (e.g., response posts). Responses can be generally available to other users of the social network 116 (e.g., public response posts in the forum) or available only to certain named parties (e.g., private messages to particular users). It is desirable to provide users simplified access to responses to their posts and other content records. Accordingly, various exemplary embodiments of A physiological measurement system for use by a user include the biosensor 314 having at least one electrode responsive to an electrochemical reaction between a fluid sample and an enzyme disposed on the at least one electrode, so that the biosensor provides a signal corresponding to a physiological parameter in the form of an analyte concentration in the fluid sample. The processor 386 is connected to the biosensor and configured to receive the signal from the biosensor and automatically determine analyte data using the signal. The network interface 315 is connected to the processor 386 and configured to selectively convey data bidirectionally between the processor and a social network via the communications link 316. The storage device 340 stores credentials of the user. The user interface 330 is operative to present information to the user, e.g., via display.

The processor 386 retrieves the credentials from the storage device 340, e.g., by carrying out stored program instructions as discussed above. The processor 386 transmits the credentials and the analyte data to the social network 116. The processor 386 then retrieves from the social network 116 response data corresponding to the transmission. The response data correspond to a second user (human or not) that is different from the user. The processor 386 presents an indication of the response data using the user interface. The indication can inform the user that a response is available, or can provide part or all of the content of one or more response(s). The indication can be visible (e.g., an LED or pop-up message on the touchscreen 144, FIG. 1, known in the mobile-device user-interface art as a "toast notification"), audible (e.g., a beep or ringtone), mechanical (e.g., a vibration), or another indication.

In various embodiments, the storage device 340 is configured to store respective credentials of the user on a plurality of social networks. The processor 386 transmits the analyte data and the stored respective credential to each of the plurality of social networks, and awaits the response data from any of the plurality of social networks. The processor 386 can be configured to poll the social networks periodically or to await push updates sent by one or more of the social networks (e.g., automated email notifications).

Responses to forum posts can come seconds after posting, decades after posting, or anywhere in between. Accordingly, in various embodiments, the processor 386 is configured to receive from the social network 116 an identifier corresponding to the transmission. The identifier can be, e.g., a standard Internet Message-ID, or a pair of integers (forum-ID, post-ID). The processor 386 can store the received identifier in volatile or nonvolatile storage in the storage device 340. The processor 386 delays a selected length of time, e.g., by sleeping or by scheduling an event to occur after the delay time. After the delay, the processor 386 transmits a query, including the identifier, to the social network 116 to determine whether the response data is available for retrieval. The query can be, e.g., an HTTP GET with the query-string specifying the forum-ID and that posts newer than the post-ID be returned. If response data is available, the processor 386 receives from the social network 116 the response data corresponding to the transmission. The processor 386 can be configured to repeatedly query for response data, e.g., every hour or every day. The frequency of querying can be selected depending on the determined analyte data in the original transmission.

As discussed above, users of the social network 116 can be literate in one or more natural language(s). Accordingly, the processor 386 can request from the social network 116 response data limited to data in one or more selected language(s). Continuing the example above, the processor 386 can transmit the query can include one or more ISO 639-1 language codes, e.g., "responselang=gd" to request only Scottish Gaelic response data, or "responselang=gd,en" to request Scottish Gaelic or English response data.

In the particular example described herein, analyte data is often categorized as preprandial (before meal) or postprandial (after meal). This categorization is an example of supplemental data that may correspond to the determined analyte data. For example, the glucose meter 114, FIG. 1, can prompt the subject 1138 to select whether a just-taken BG reading was preprandial, postprandial, or neither (e.g., more than two hours away from any meal). Users may want to communicate supplemental data to the social network 116 to help other users understand the significance of the determined BG data. In various embodiments, therefore, the processor 386 is configured to receive supplemental data corresponding to the signal via the user interface 330. The processor 386 transmits the supplemental data to the social network 116 with the determined analyte data.

In various embodiments, the processor 386 is in a smartphone or similar device. Specifically, the network interface 315 includes a cellular interface, and the user interface 330 includes a touchscreen 144, FIG. 1. A first housing 130 holds the processor 386, the network interface 315, the user interface 330, and a first connector 328. A second housing 131, FIG. 1, separate from the first housing 130 holds the biosensor 314 and a second connector 329 selectively attachable to the first connector 328. The processor 386 receives the signal from the biosensor 314 via the first and second connectors 328, 329 when the first and second connectors 328, 329 are attached together.

In various aspects, the system includes a mechanical alerting device 327 (represented graphically as a speaker icon). The mechanical alerting device 327 can be, e.g., a speaker (as shown) or a buzzer or vibration source (e.g., a motor having an asymmetrical weight on its shaft). The processor 386 provides an alert via the mechanical alerting device 327 when the response data is retrieved.

Figure 4A:
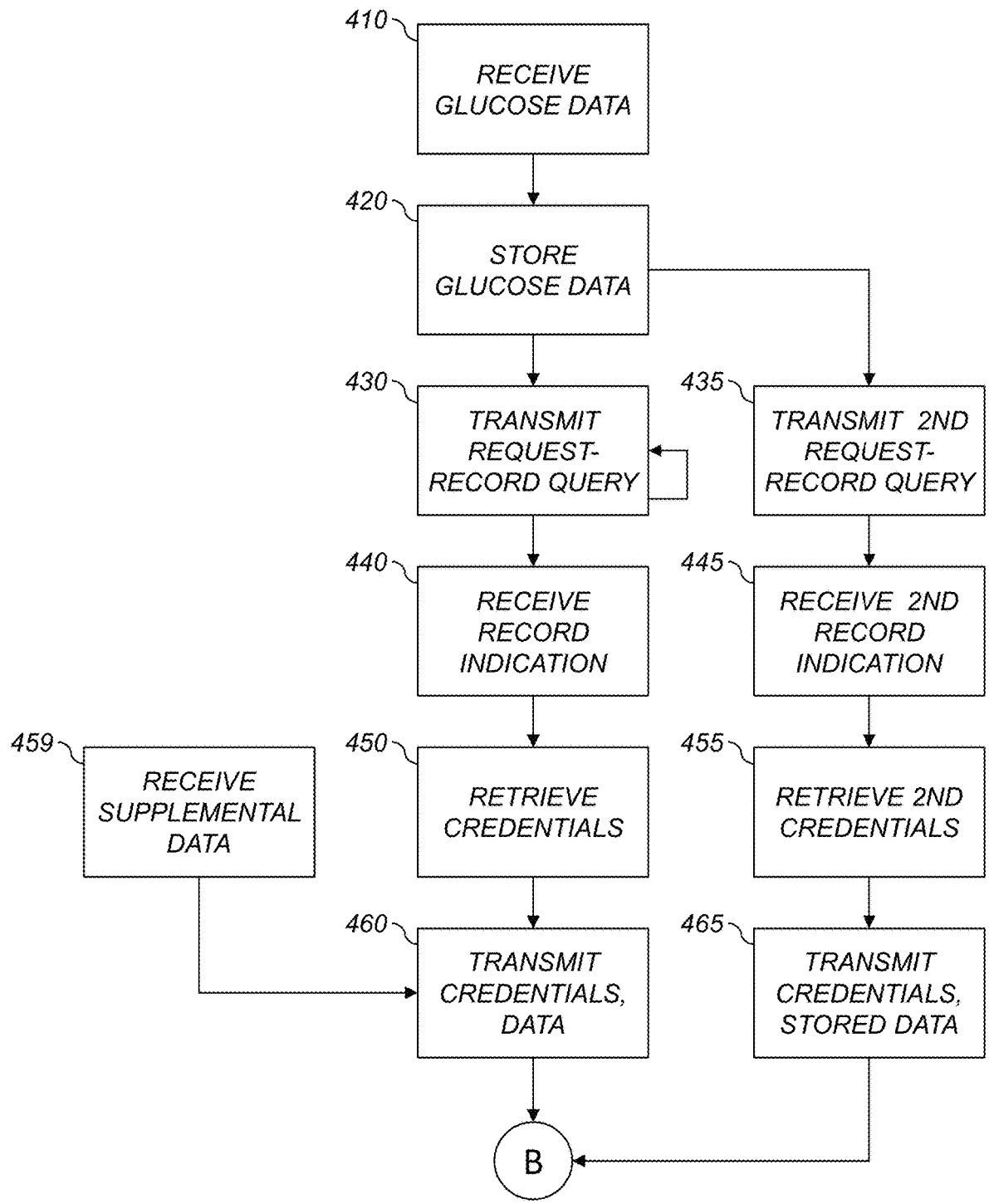
FIGS. 4A-4B are a flowchart illustrating an exemplary method for processing analyte data.
Figure 4B:
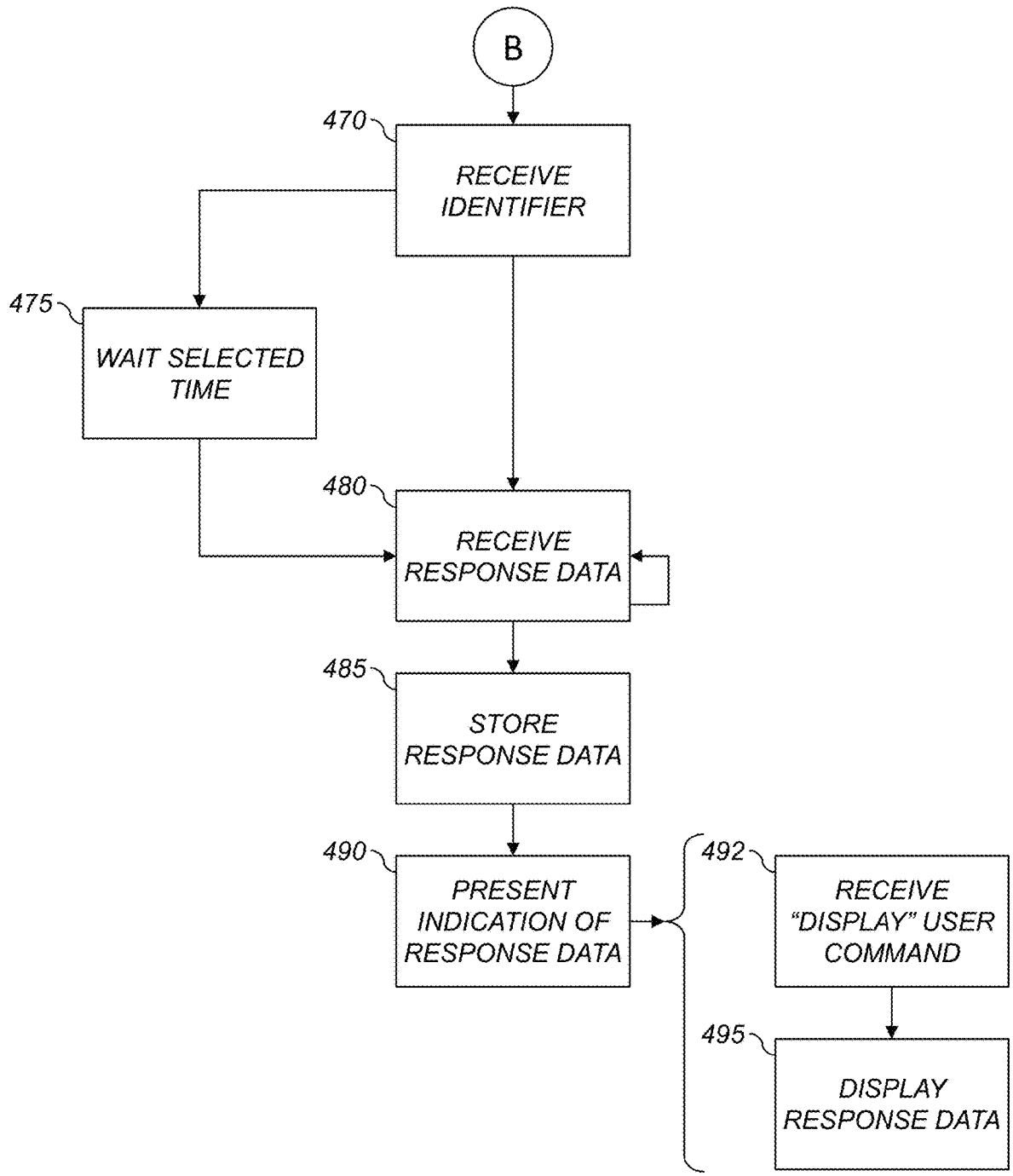

FIGS. 4A-4B are a flowchart illustrating an exemplary method for processing analyte data. The steps can be performed in any order except when otherwise specified, or when data from an earlier step is used in a later step. For purposes of this exemplary method, processing begins with step 410. For clarity of explanation, reference is herein made to various components shown in FIGS. 1-3 that can carry out or participate in the steps of the exemplary method. For example, the steps of method can be automatically performed using the processor 386, FIG. 3, or another data processing system. It should be noted, however, that other components can be used; that is, the exemplary method is not limited to being carried out by the identified components.

In step 410, analyte data of a user is received from a biosensor that detects an analyte level in a bodily fluid of the user. This can include receiving a signal from a biosensor 314 and determining the analyte data using the glucose sensor, as discussed above. Step 420 can be next.

In step 420, the received analyte data is stored in a storage device, volatile or nonvolatile. The data can be stored in the storage device 340. Step 430 can be next.

In step 430, a query for analyte-data-request records is transmitted to a social network 116. Queries and analyte-data-request records are described above. The query can request "what is your analyte level (e.g., blood-glucose)?" and similar posts be identified. Step 440 can be next.

In step 440, an indication of an analyte-data-request record is received from the social network. The indication can be data indicating, e.g., "there are 5 post(s) matching your query." Step 450 can be next.

If the social network 116, FIG. 1, is not able to locate any analyte-data-request records corresponding to the query, the social network may simply not respond to the transmitted query, or may respond to the transmitted query with a negative acknowledge (NAK) or similar indication that the query was valid, but no records were found. In various embodiments, step 430 is repeated periodically to try to locate records. For example, the query can be re-transmitted every n minutes, e.g., n=5. If the query includes a timestamp or other time limitation, that element of the query can be updated with each retransmission.

In step 450, credentials of the user are retrieved from the storage device. Credentials are described above. Step 460 can be next.

In step 460, in response to the received indication, the credentials and the stored analyte data are transmitted to the social network. The method can end here, or step 460 can be followed by step 470, FIG. 4B.

In various embodiments, a processor communicates with multiple social networks. In an example, step 420 is followed by steps 430 and 435. Steps 430, 440, 450, and 460 can be performed in parallel with steps 435, 445, 455, and 465, or one of those groups of steps can be performed before the other.

In step 435, a query for analyte-data-request records is transmitted to a second social network. The second social network can be a different social network from the social network 116. Step 445 can be next.

In step 445, an indication of an analyte-data-request record is received from the second social network. Step 455 can be next.

In step 455, second credentials of the user are retrieved from the storage device 340. The second credentials correspond to the second social network. The credentials and the second credentials can be the same or different. Step 465 can be next.

In step 465, in response to the received indication from the second social network, the second credentials and the stored analyte data are transmitted to the second social network. Step 465 can be followed by step 470.

In various embodiments, supplemental data are provided, e.g., by the subject 1138. In step 459, the supplemental data are received. Then, in step 460, the supplemental data are automatically transmitted with the stored analyte data to the social network. Step 459 can include automatically querying the user for the supplemental data via the user interface 330. The supplemental data can include meal data corresponding to the analyte data. Meal data can include a pre- or postprandial indication, or data about a meal the subject 1138 has consumed or will consume. For example, meal data for a postprandial BG reading can include the number of grams of carbohydrates (CHO) consumed at the meal. The supplemental data can also include tag data, pattern data, or comments.

Referring to FIG. 4B, in at least one embodiment, after transmitting the credentials and the stored analyte data (step 460, FIG. 4A), a corresponding identifier is received from the social network 116 in step 470. Identifiers (e.g., post numbers) are discussed above. Step 475 or step 480 can be next. In step 475, the processor waits a selected time after receiving the identifier (step 470) and before retrieving the response data (step 480).

In step 480, response data corresponding to the received identifier are received from the social network 116. The response data correspond to a second user (human or not) different from the user. The response data can be, e.g., an encouraging content record (e.g., "good job!"), a solicitous content record (e.g., "are you OK?"), or an indication that a response content record is available. As discussed above with reference to step 430, the social network 116 can omit to respond, or respond NAK, if no response data are available. Step 480 can be repeated periodically, e.g., every minute or every t minutes, t>1, until response data are available. In optional step 485, the response data are stored in the storage device 340. If the response data are an indication that a response content record is available, step 485 can include retrieving the response content record from the social network and storing the retrieved response content record in the storage device 340. Step 490 can be next.

In step 490, an indication of the response data is presented. The indication can be presented to the user visually, audibly, or otherwise. Examples are described above.

In various aspects, step 490 includes steps 492 and 495. In step 492, a user command to display response data is received. This can be, e.g., a user's pressing a command button in the user interface 330. In response to the user command, in step 495, at least some of the stored response data is displayed on a display.

In view of the foregoing, embodiments of the invention provide improved communication of blood analyte data. Various embodiments facilitate interactions between users via social networks. Various embodiments advantageously integrate social-media communications into episodic blood glucose meters or into smartphone apps that communicate with episodic blood glucose meters. This permits users to measure and discuss their analyte (e.g., blood glucose) results from a single device instead of from two separate devices between which the users are required to manually copy data. A technical effect of various processing carried out by biosensors and processors described herein is to convert glucose levels in a blood sample to data and communicate those data outside the particular computing device that performed the conversion, then to facilitate communication between a human user and another human regarding the data. Another technical effect is to request information from a social network about blood analyte data the user will provide to the social network (e.g., to query for analyte-data-request records) or has provided to the social network (e.g., to query for response data).

PARTS LIST FOR FIGS. 1-4B

100 physiological measurement
102 drug delivery device
104 controller
106 infusion set
108 flexible tubing
112 radio frequency communications link
114 glucose meter
115 test strip
116 social network
117 radio frequency communications link
118 wireless communication network
125 test strip
126 server
128 storage device
130, 131 housings
144 touchscreen
200 test strip
201, 202 contact pads
204 substrate
210, 220 electrodes
230 sample-receiving chamber
314 biosensor
315 network interface
316 communications link 320 peripheral system
322 glucose sensor
325 insulin delivery device
327 mechanical alerting device
328, 329 connectors
330 user interface
340 storage device
341 memory
342 disk
386 processor
410, 420, 430, 435, 440 steps
445, 450, 455, 459, 460 steps
465, 470, 475, 480, 485 steps
490, 492, 495 steps
1138 subject While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Separate references to "an embodiment" or "particular embodiments" or the like do not necessarily refer to the same embodiment or embodiments; however, such embodiments are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted. To the extent there are variations of the invention that are within the spirit of the disclosure or are equivalent to the inventions found in the claims, it is the intent that this patent will cover those variations as well.

What is claimed is:

1. A glucose measurement system comprising:
   a) a biosensor having at least one electrode responsive to an electrochemical reaction between a fluid sample and an enzyme disposed on the at least one electrode, so that the biosensor provides a signal corresponding to a glucose concentration in the fluid sample;
   b) a processor connected to the biosensor and programmed with instructions to receive the signal from the biosensor and automatically determine the glucose concentration using the signal;
   c) a network interface connected to the processor that selectively conveys glucose concentration data between the processor and at least one social network via a communications link in which the processor is programmed with instructions to transmit a query string for analyte-data-request records to the at least one social network wherein an analyte-data-request record is a forum post stored on the at least one social network soliciting glucose information including specific values or trend information from subjects, receive an indication of at least one said analyte-data-request record being present on the at least one social network requesting glucose concentration data, transmit the glucose concentration data to the at least one social network in response to the at least one analyte-data-request record, receive an identifier from the at least one social network, and retrieve response data from the at least one social network based on the transmitted glucose concentration data, wherein the processor is programmed to wait a selected period of time after receiving the identifier before retrieving the response data; and
   d) a drug delivery device in communication with the processor and configured to receive glucose concentration data from the processor and automatically deliver an amount of insulin to a user based on the glucose concentration data.

2. The system according to claim 1, further including a storage device that stores user credentials, wherein the processor is further programmed with instructions to retrieve user credentials from the storage device and transmit the user credentials to the at least one social network in association with the transmission of the requested glucose concentration data.

3. The system according to claim 1, further including a user interface and a storage device for storing respective user credentials for a plurality of social networks, wherein the processor is further programmed with instructions to present a menu of the plurality of social networks to a user of the system via the user interface, receive a selection of one of the plurality of social networks via the user interface, receive the user credentials corresponding to the selection from the storage device, and transmit the retrieved user credentials with the requested glucose concentration data.

4. The system according to claim 1, further including a user interface and a housing holding the biosensor, the processor, the network interface, and the user interface.

5. The system according to claim 1, further including:
   a) a user interface;
   b) a first connector and a second connector selectively attachable to the first connector;
   c) a first housing holding the processor, the network interface, the user interface, and the first connector; and
   d) a second housing separate from the first housing holding the biosensor and the second connector, in which the processor is programmed to receive the signal from the biosensor via the first and second connectors when the first and second connectors are attached together.

6. The system according to claim 5, wherein the network interface comprises a cellular interface and the user interface comprises a touchscreen.

7. The system according to claim 1, wherein the processor is further programmed with instructions to automatically send queries to one or more social networks about a type of glucose concentration data the user will provide, to receive indications from the one or more social networks regarding the type of glucose concentration data that is requested, and to transmit the determined glucose concentration data to the one or more social networks in response to the indications.

8. The system according to claim 1, wherein the glucose concentration data requested is limited to one or more selected languages.

9. A glucose measurement system for use by a user, the system comprising:
   a) a biosensor having at least one electrode responsive to an electrochemical reaction between a fluid sample and an enzyme disposed on the at least one electrode, so that the biosensor provides a signal corresponding to a glucose concentration in the fluid sample;
   b) a processor connected to the biosensor and programmed with instructions to receive the signal from the biosensor and automatically determine the glucose concentration in the fluid sample using the signal;
   c) a network interface connected to the processor that selectively conveys glucose concentration data between the processor and at least one social network via a communications link;

d) a storage device for storing credentials of the user;

e) a user interface operative to present information to the user, wherein the processor is further programmed to transmit a query for analyte-data-request records from the at least one social network in which an analyte-data-request is a stored forum post on the at least one social network soliciting blood glucose information including specific values or trend information of a subject, and receive an indication of said analyte-data-request records from the at least one social network, the processor being further programmed to retrieve the credentials from the storage device, and transmit the credentials and requested glucose concentration data to the at least one social network in response to a said analyte-data-request record that is received from the at least one social network, retrieve from the at least one social network a response relating to the transmitted glucose concentration data, the response corresponding to a second user different from the user, and present an indication of the response using the user interface; and f) a drug delivery device in communication with the processor and configured to receive the glucose concentration data from the processor and automatically deliver an amount of insulin to the user based on the glucose concentration data.

10. The system according to claim 9, in which the storage device stores respective credentials of the user on a plurality of social networks, wherein the processor is programmed with instructions to transmit the requested glucose concentration data and the stored respective credential to each of the plurality of social networks, and await the response data from any of the plurality of social networks, the response glucose concentration data corresponding to a second user that is different than the user.

11. The system according to claim 9, in which the processor is programmed with instructions to receive an identifier from the at least one social network, the identifier corresponding to the transmission, delay a selected length of time, and transmit a query including the identifier to the at least one social network to determine whether the response data is available for retrieval.

12. The system according to claim 9, in which the processor is programmed with instructions to receive supplemental data corresponding to the signal via the user interface and transmit the supplemental data to the at least one social network with the requested glucose concentration data.

13. The system according to claim 9, the network interface comprising a cellular interface, the system further including:

a) a touchscreen;

b) a first connector and a second connector selectively attachable to the first connector;

c) a first housing holding the processor, the network interface, the user interface, and the first connector; and d) a second housing separate from the first housing holding the biosensor and the second connector, wherein the processor is programmed with instructions to receive the signal from the biosensor via the first and second connectors when the first and second connectors are attached together.

14. The system according to claim 13, further including a mechanical alerting device, wherein the processor is programmed with instructions to provide an alert via the mechanical alerting device when the glucose concentration data is retrieved.

15. The system according to claim 9, wherein the processor is further programmed with instructions to automatically send queries to one or more social networks about a type of glucose concentration data the user will provide, to receive indications from the one or more social networks regarding the type of glucose concentration data that is requested, and to transmit the determined glucose concentration data to the one or more social networks in response to the indications.

16. The system according to claim 9, wherein the glucose concentration data requested is glucose concentration data that is limited to one or more selected languages.

* * * * *